United States Patent
MacFarland et al.

(10) Patent No.: US 10,317,386 B2
(45) Date of Patent: Jun. 11, 2019

(54) DETERMINATION OF AQUEOUS NITRATE CONCENTRATION

(71) Applicant: Hach Company, Loveland, CO (US)

(72) Inventors: Darren Kent MacFarland, Windsor, CO (US); Angella Nicholle Greenawalt, Fort Collins, CO (US)

(73) Assignee: HACH COMPANY, Loveland, CO (US)

( * ) Notice: Subject to any disclaimer, the term of this patent is extended or adjusted under 35 U.S.C. 154(b) by 201 days.

(21) Appl. No.: 15/223,708

(22) Filed: Jul. 29, 2016

(65) Prior Publication Data

US 2018/0031536 A1  Feb. 1, 2018

(51) Int. Cl.
| | |
|---|---|
| *G01N 33/00* | (2006.01) |
| *G01N 33/18* | (2006.01) |
| *C07C 323/20* | (2006.01) |
| *C07D 235/08* | (2006.01) |
| *C07C 323/33* | (2006.01) |
| *C08G 65/40* | (2006.01) |
| *G01N 21/29* | (2006.01) |
| *G01N 21/25* | (2006.01) |
| *G01N 21/27* | (2006.01) |
| *G01N 21/31* | (2006.01) |

(52) U.S. Cl.
CPC ......... *G01N 33/188* (2013.01); *C07C 323/20* (2013.01); *C07C 323/33* (2013.01); *C07D 235/08* (2013.01); *C08G 65/40* (2013.01); *G01N 21/251* (2013.01); *G01N 21/27* (2013.01); *G01N 21/293* (2013.01); *G01N 21/31* (2013.01)

(58) Field of Classification Search
CPC .................................................... G01N 33/188
USPC ......................................................... 436/110
See application file for complete search history.

(56) References Cited

U.S. PATENT DOCUMENTS

| | | | |
|---|---|---|---|
| 2012/0021527 A1* | 1/2012 | Salzer ..................... | G01N 21/78 436/163 |
| 2014/0065606 A1* | 3/2014 | Green ..................... | G01N 33/84 435/6.1 |

* cited by examiner

*Primary Examiner* — Christine T Mui
*Assistant Examiner* — Emily R. Berkeley
(74) *Attorney, Agent, or Firm* — Ference & Associates LLC

(57) ABSTRACT

A method of measuring nitrate concentration in an aqueous sample includes mixing the aqueous sample with a water-soluble thioether chosen to reduce nitrate in the aqueous sample to nitrite in the presence of a water soluble catalyst, and a water soluble reagent system adapted to interact with nitrite to generate a color; measuring color generation, and correlating the color generation to nitrate concentration.

20 Claims, 6 Drawing Sheets

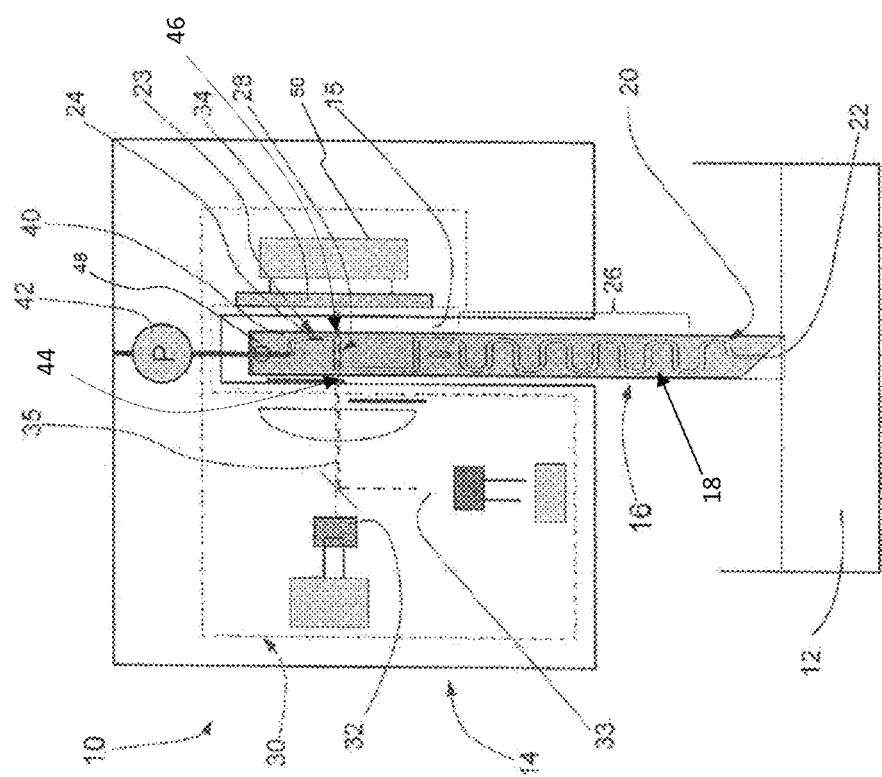

DETERMINATION OF AQUEOUS NITRATE CONCENTRATION

BACKGROUND

The following information is provided to assist the reader in understanding technologies disclosed below and the environment in which such technologies may typically be used. The terms used herein are not intended to be limited to any particular narrow interpretation unless clearly stated otherwise in this document. References set forth herein may facilitate understanding of the technologies or the background thereof. The disclosure of all references cited herein are incorporated by reference.

Determination of aqueous nitrate concentration is important for a variety of public and commercial applications. Nitrate is a common contaminate in water, and high quantities of nitrates in drinking water can be harmful to people and animals. Thus, there is a need to carefully monitor nitrate levels in water. Limits on acceptable nitrate concentration have been established for drinking water. Nitrate concentrations may, for example, be monitored in drinking water supplies, sewage, waste water, water remediation, biological samples, sea water, etc.

Methodologies for measuring aqueous nitrate concentration include spectrophotometry, colorimetry, chromatography, ion selective electrodes, etc. Various shortcomings exist with these methods including toxicity of reagents, cost, sensitivity, selectivity, variability, range, stability, time requirements, portability, etc.

In a number of colorimetric nitrate tests, nitrate is first reduced to nitrite, followed by nitrite analysis. Typically, reduction of nitrate to nitrite is accomplished using cadmium. Then, nitrite concentration is determined using the Griess assay or test. Nitrate concentration is directly related to nitrite concentration. However, cadmium may be toxic and is likely to be prohibited for use in water testing. Moreover, shaking is required in cadmium-containing systems, which may affect the surface reaction that occurs in the use of cadmium to reduce nitrate to nitrite, resulting in variability in testing. Zinc has also been used as a reductant in the nitrate test, but Zn is not as selective as Cd and can result in over-reduction of the nitrate to NO.

Portable water testing equipment such as the PORTABLE PARALLEL ANALYZER™ (available from Hach Company of Loveland, Colo.) has been introduced in which the test reagents are deposited (dried) upon a test element (for example, the CHEMKEY® test element available from Hach Company) that can be easily inserted into the equipment and utilized in field testing. The nature of the test elements and associated equipment limit or prevent the use of solid reagents. In that regard, water soluble reagents of an analysis system are dried upon the test element. Insoluble solids are difficult to deposit on test elements/chips. Solid reagents in nitrate testing, such as cadmium and zinc, cannot be used in such testing equipment.

The sulfoxidation of thioethers with nitrate as the oxidant and a homogeneous Mo/Cu(II) co-catalyst system has been reported as a pathway to sulfoxides in organic solvent such as acetonitrile. A variety of thioethers were shown to undergo the reaction to a greater or lesser extent. Organic-soluble thioether reagents and catalysts were also shown to be suitable for detection of nitrates in certain environments.

SUMMARY

A method of measuring nitrate concentration in an aqueous sample includes mixing the aqueous sample with a water-soluble thioether chosen to reduce nitrate in the aqueous sample to nitrite in the presence of a water soluble catalyst, and a water soluble reagent system adapted to interact with nitrite to generate a color; measuring color generation, and correlating the color generation to nitrate concentration. The water soluble thioether may, for example, be a thioether-containing five-membered, aromatic heterocyclic compound, a phenylalkyl thioether or a substituted phenylalkyl thioether. In a number of embodiments, the water soluble thioether has the formula:

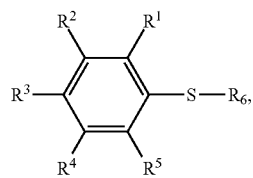

wherein $R^1$, $R^2$, $R^3$, $R^4$, and $R^5$ are selected independently from H, and a hydrophilic group or electron density donating group, wherein at least one of $R^1$, $R^2$, $R^3$, $R^4$, and $R^5$ is a hydrophilic and electron density donating group, and wherein $R^6$ is selected from the group consisting of a $C_1$-$C_6$ alkyl group or a hydrophilic polymer. In a number of embodiments, two or more of $R^1$, $R^2$, $R^3$, $R^4$, and $R^5$ are independently selected from a hydrophilic group and an electron density donating group. In a number of embodiment, one or more (for example, one, two or three) of $R^1$, $R^2$, $R^3$, $R^4$, and $R^5$ are substituent groups which are both hydrophilic and electron density donating. The hydrophilic polymer of $R^6$ may, for example, be a polyalkyleneoxide (for example, a polyethylene glycol or PEG). The polyalkyleneoxide may, for example, include 4 to 1000 carbon atoms.

In a number of embodiments, at least one of $R^1$, $R^2$, $R^3$, $R^4$, and $R^5$ is —$OR^a$ wherein $R^a$ is selected from the group consisting of H, a $C_1$-$C_6$ alkyl group, a $C_1$-$C_6$ sulfonate terminated alkyl group, a phenyl group, and a polyalkylene oxide group, —$NR^bR^c$ wherein $R^b$ and $R^c$ are selected independently from the group consisting of H, a $C_1$-$C_6$ alkyl group, a $C_1$-$C_6$ sulfonate terminated alkyl group, and a polyalkylene oxide group, a dihydroxybenzene group, a phenyl diamine group, a phenyl diether group, a carboxylate group (—C(O)OH) and a polyalkyleneoxide group; or $R^1$ and $R^2$ together form a chain of four or five members selected from the group of CH, $CH_2$, NH, CC(O)OH or $NR^d$, wherein $R^d$ is an $C_1$-$C_6$ alkyl group or $C_1$-$C_6$ sulfonate terminated alkyl group; or $R^3$ and $R^4$ together form a chain of four or five members selected from the group of CH, $CH_2$, NH, CC(O)OH or $NR^d$. Such chains may, for example, be conjugated systems. The phenyl diamine may have, for example, the formula $C_6H_3(N(R^7)_2)(N(R^8)_2)$, wherein $R^7$ and $R^8$ are independently selected from the group consisting of hydrogen, $C_1$-$C_6$ alkyl group, a sulfonate terminated $C_1$-$C_6$ alkyl group, or a polylakyleneoxide group. The phenyl diether may, for example, have the formula)) $C_6H_3(O(R^9))(O(R^{10}))$, wherein $R^9$ and $R^{10}$ are independently selected from the group consisting of hydrogen, $C_1$-$C_6$ alkyl group, a sulfonate terminated $C_1$-$C_6$ alkyl group, or a polylakyleneoxide group. Polyakyleneoxide groups (for example, PEG groups) in substituents hereof may, for example, include 4 to 1000 carbon atoms.

The water soluble catalyst may, for example, be or include $MoO_2Cl_2(L)_2$, wherein L is a hydrophilic phosphine group. L may for example, be a triphenylphosphineoxide group or a trisulfonated-triphenylphosphineoxide. The water soluble catalyst further include a co-catalyst such as a $Cu^{2+}$ co-catalyst.

The water soluble reagent system may, for example, be a Griess reagent system. The water soluble reagent system may, for example, include aniline or an aniline derivative and a receptor species chosen to form a chromophore with nitrite. The aniline derivative may, for example, be chosen to form a diazonium salt with nitrite. The aniline derivative may, for example, be sulphanilic acid. In a number of embodiments, the receptor species includes an azo dye agent. The receptor species may, for example, be chosen from the group consisting of N-alpha-naphthyl-ethylenediamine, genistic acid, and chromotropic acid.

In a number of embodiments, the color generation occurs in the visible light spectrum. The color generation may, for example, be measured using a spectrometer, colorimeter, photometric device, color disc, color block, or the like. In a number of embodiments, the range of nitrate detection is between about 0 and 15 ppmw.

A water soluble thioether has the formula:

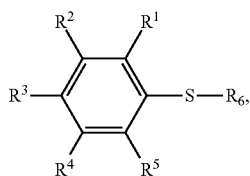

wherein $R^1$, $R^2$, $R^3$, $R^4$, and $R^5$ are selected independently from H, a hydrophilic group or an electron density donating group, wherein at least one of $R^1$, $R^2$, $R^3$, $R^4$, and $R^5$ is a hydrophilic group or an electron density donating group, and wherein $R^6$ is selected from the group consisting of a $C_1$-$C_6$ alkyl group or a hydrophilic polymer.

In a number of embodiments, two or more of $R^1$, $R^2$, $R^3$, $R^4$, and $R^5$ are independently selected from a hydrophilic group and an electron density donating group. In a number of embodiment, one or more (for example, one, two or three) of $R^1$, $R^2$, $R^3$, $R^4$, and $R^5$ are substituent groups which are both hydrophilic and electron density donating. The hydrophilic polymer of $R^6$ may, for example, be a polyalkyleneoxide (for example, a polyethylene glycol or PEG). The polyalkyleneoxide may, for example, include 4 to 1000 carbon atoms.

In a number of embodiments, at least one of $R^1$, $R^2$, $R^3$, $R^4$, and $R^5$ is an amine group, —$OR^a$ wherein $R^a$ is selected from the group consisting of H, a $C_1$-$C_6$ alkyl group, a $C_1$-$C_6$ sulfonate terminated alkyl group, a phenyl group, and a polyalkylene oxide group, —$NR^bR^c$ wherein $R^b$ and $R^c$ are selected independently from the group consisting of H, a $C_1$-$C_6$ alkyl group, a $C_1$-$C_6$ sulfonate terminated alkyl group, and a polyalkylene oxide group, a dihydroxybenzene group, a phenyl diamine group, a phenyl diether group, a carboxylate group and a polyalkyleneoxide group; or $R^1$ and $R^2$ together form a chain of four or five members selected from the group of CH, $CH_2$, NH, CC(O)OH or $NR^d$, wherein $R^d$ is an $C_1$-$C_6$ alkyl group or $C_1$-$C_6$ sulfonate terminated alkyl group; or $R^3$ and $R^4$ together form a chain of four or five members selected from the group of CH, $CH_2$, NH, CC(O) OH or $NR^d$. Such chains may, for example, be conjugated systems. The phenyl diamine may, for example, the formula $C_6H_3(N(R^7)_2)(N(R^8)_2)$, wherein $R^7$ and $R^8$ are independently selected from the group consisting of hydrogen, $C_1$-$C_6$ alkyl group, a sulfonate terminated $C_1$-$C_6$ alkyl group, or a polyalkyleneoxide group. The phenyl diether may, for example, have the formula $C_6H_3(O(R^9))(O(R^{10}))$, wherein $R^9$ and $R^{10}$ are independently selected from the group consisting of hydrogen, $C_1$-$C_6$ alkyl group, a sulfonate terminated $C_1$-$C_6$ alkyl group, or a polyalkyleneoxide group. Polyakyleneoxide groups (for example, PEG groups) in substituents hereof may, for example, include 4 to 1000 carbon atoms.

In a number of embodiments in which one of $R^1$, $R^2$, $R^3$, $R^4$, and $R^5$ is an amine group or a hydroxyl group or in which one of $R^1$, $R^2$, $R^3$, $R^4$, and $R^5$ is an amine group and one of $R^1$, $R^2$, $R^3$, $R^4$, and $R^5$ is a hydroxyl group, another of $R^1$, $R^2$, $R^3$, $R^4$, and $R^5$ is not H or $R^6$ is not $CH_3$.

A kit for measuring aqueous nitrate concentration includes an analysis system including a water soluble thioether chosen to reduce nitrate in the aqueous sample to nitrite, a water soluble catalyst, and a water soluble reagent system adapted to react with nitrite to generate a color; a system to measure a color generation, and a system to correlate the color generation to nitrate concentration. The water soluble thioether, the water soluble reagent system and the system to measure color generation may be those described above. The color generation may, for example, occur in the visible light spectrum. The color generation may, for example, be measured using a spectrometer, colorimeter, photometric device, color disc, color block, or the like. The range of nitrate detection may, for example, be between about 0 and 15 ppmw.

A kit for measuring aqueous nitrate concentration includes analysis system including a water soluble thioether chosen to reduce nitrate in the aqueous sample to nitrite, a water soluble catalyst, and a water soluble reagent system adapted to react with nitrite to generate a color. The analysis system components (the water soluble thioether, the water soluble catalyst, and the water soluble reagent system) may, for example, be deposited on a test element which is insertable into an analyzer.

An analysis system includes a mixture of a water soluble thioether chosen to reduce nitrate in the aqueous sample to nitrite, a water soluble catalyst, and a water soluble reagent system adapted to react with nitrite to generate a color.

The present kits, systems, methods and compositions, along with the attributes and attendant advantages thereof, will best be appreciated and understood in view of the following detailed description taken in conjunction with the accompanying drawings.

BRIEF DESCRIPTION OF THE DRAWINGS

FIG. 6 illustrates an embodiment of a kit including a portable analyzer and a test element.

DETAILED DESCRIPTION

Figure 1:
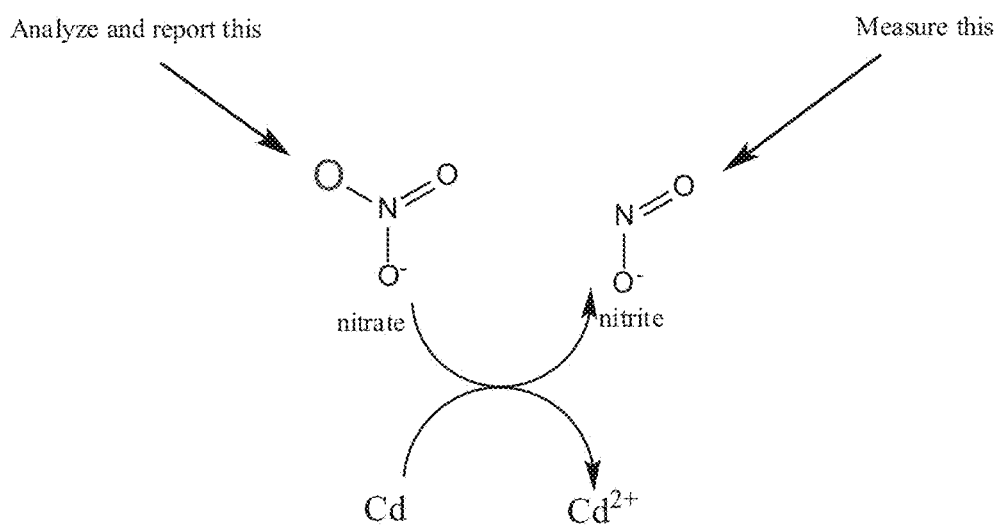
FIG. 1 illustrates reduction of nitrate to nitrite using cadmium reductant.

It will be readily understood that the components of the embodiments, as generally described and illustrated in the figures herein, may be arranged and designed in a wide variety of different configurations in addition to the described representative embodiments. Thus, the following more detailed description of the representative embodiments, as illustrated in the figures, is not intended to limit the scope of the embodiments, as claimed, but is merely illustrative of representative embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

As used herein and in the appended claims, the singular forms "a," "an", and "the" include plural references unless the context clearly dictates otherwise. Thus, for example, reference to "a thioether" includes a plurality of such thioethers and equivalents thereof known to those skilled in the art, and so forth, and reference to "the thioether" is a reference to one or more such thioethers and equivalents thereof known to those skilled in the art, and so forth. Recitation of ranges of values herein are merely intended to serve as a shorthand method of referring individually to each separate value falling within the range. Unless otherwise indicated herein, and each separate value, as well as intermediate ranges, are incorporated into the specification as if individually recited herein. All methods described herein can be performed in any suitable order unless otherwise indicated herein or otherwise clearly contraindicated by the text.

In a number of embodiments hereof, water-soluble thioethers are synthesized for use in, for example, nitrate detection. In a number of methods hereof for aqueous nitrate detection, water-soluble thioethers are sacrificially oxidized to the corresponding sulfoxide while nitrate is reduced to nitrite in the presence of a water-soluble catalyst system (for example, a water-soluble molybdenum (Mo) catalyst system). The nitrite produced may, for example, be analyzed using a water-soluble reagent system such as the Griess assay system and correlated to nitrate concentration. In a number of other embodiments, kits for the determination of aqueous nitrate concentration based on the thioether chemistry described above are provided. In a number of embodiments hereof, the water-soluble reagents and catalysts hereof are deposited on test elements, stored, and later used with a portable analysis system. Thus, the analysis systems hereof are, for example, readily used with analysis systems such as the PORTABLE PARALLEL ANALYZER™ and corresponding CHEMKEY® test elements of Hach Company.

In a number of embodiments, the water soluble thioethers hereof are water-soluble phenylthioethers. The reaction kinetics and water solubility of the phenylthioethers can be tailored via targeted attachments of substituents to the phenyl ring. By using phenyl ring attachments that differ in hydrophilicity, the water solubility of the phenylthioethers is adjustable. By using phenyl ring substituents that differ in electron density, the reactivity/reaction kinetics (oxidizability, oxygen transfer ability and reaction rate) of the thioether compound are adjustable.

Advantages of the reagents, methods and kits hereof for nitrate determination (as compared to currently available tests) include the elimination of toxic metals, the elimination of vigorous shaking to mix solids, the water solubility of all method components, the ability to deposit all test components on a test element to be later used in portable analysis systems, high selectivity of nitrite production, the ability to tailor the reaction rate via the substituents of the thioether, and the ability to tailor the water-solubility of the thioether.

Figure 2:
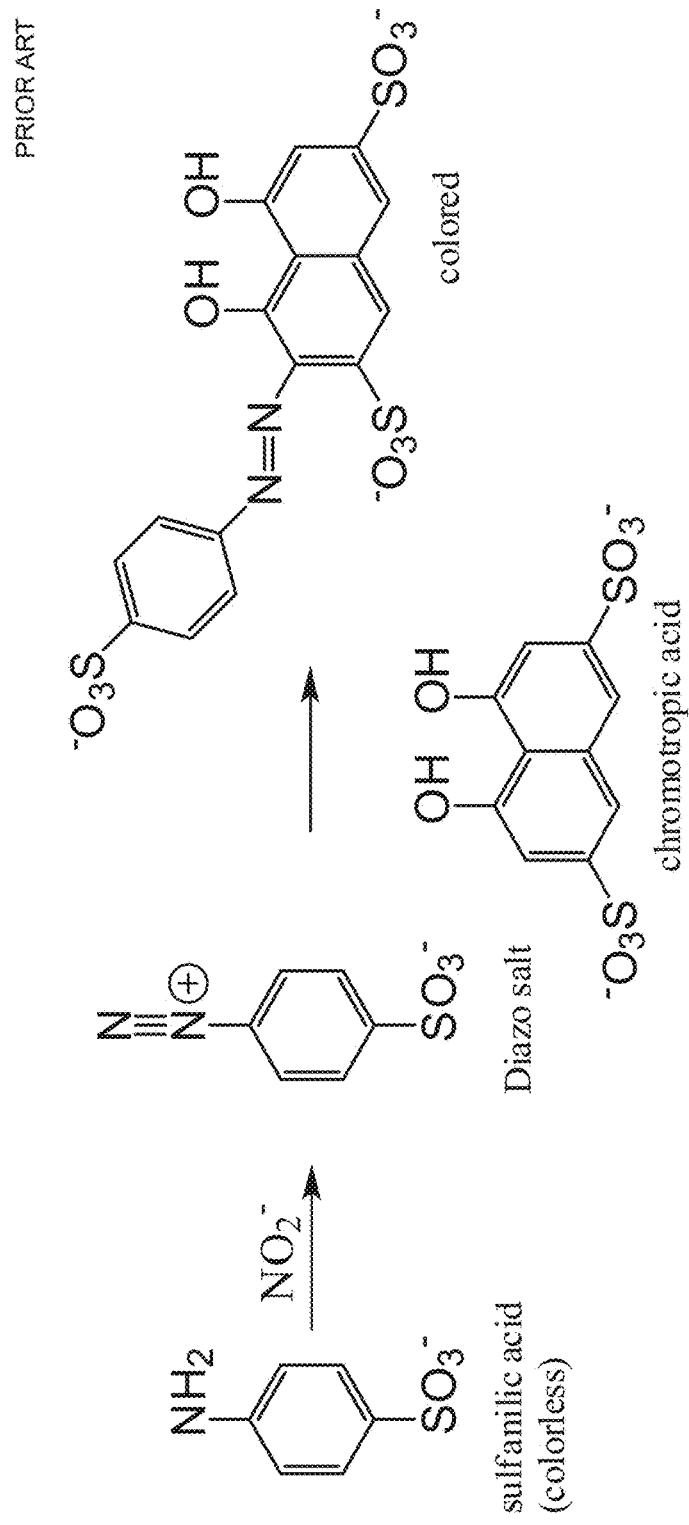
FIG. 2 shows an example of the Griess reagent and test.

As described above, there are several methods for the determination of aqueous nitrate concentration. The colorimetric method is very widely used as a result of its ease and portability. In many colorimetric nitrate tests, nitrate is first reduced to nitrite, followed by nitrite analysis. Typically, reduction of nitrate to nitrite is accomplished using cadmium or a similar reductant (e.g., zinc). FIG. 1 illustrates reduction of nitrate to nitrite using cadmium metal. Cadmium metal is oxidized to $Cd^{2+}$ while nitrate ($NO_3^{-1}$) is reduced to nitrite ($NO_2^{-1}$). Cd is not a catalyst, it is consumed (i.e., sacrificially) in the reaction. Nitrite concentration may, for example, be determined using the Griess assay, a representative example of which is illustrated in FIG. 2. The Griess assay refers to a class of reagents/reactions that is well known in the nitrate/nitrite detection arts. In the embodiment of the Griess assay illustrated in FIG. 2, nitrite reacts with sulphanilic acid (or another aniline derivative) in acidic solution to form a diazonium salt. The diazonium salt is then reacted with an azo dye agent (e.g., chromotropic acid) to form a colored azo dye. The color intensity produced is directly proportional to nitrite concentration, and nitrite concentration is directly related to nitrate concentration.

Zinc can alternatively be used as a sacrificial reducing agent, instead of Cd. Zn, however, is not as selective as the Cd. Zn tends to over-reduce the nitrate to NO, nitric oxide. Since NO doesn't react with sulphanilic acid in the diazotization reaction, it cannot participate in the Griess reaction and thus leads to erroneous test results. Additionally, the Zn surface is normally oxidized and requires an in-situ acid cleaning to activate it.

In the Griess reaction, nitrite ions present are reacted in an acidic medium with sulfanilic acid (or other suitable aniline derivative) to form an intermediate diazonium salt. The diazonium salt couples with an azo dye agent like chromotropic acid to form a colored product. Chronotropic acid produces a pink color upon coupling with the diazo salt. Color intensity of the compound is directly proportional to the nitrite concentration of the water sample. The measurement wavelength is 507 nm for spectrophotometers or 520 nm for colorimeters. The nitrite concentration is then directly related to nitrate concentration.

Genistic acid may, for example, be alternatively used as the azo dye agent. It produces an amber color upon coupling with the di-azo salt. Other azo dye agents may also be used. For example, if N-alpha-naphthyl-ethylenediamine is used as the azo dye agent, a pink color develops upon coupling with the di-azo salt.

The water soluble thioethers (for example, phenylthioethers) hereof may be used as sacrificial reducing agents for the determination of aqueous nitrate concentration, thereby eliminating the need for metals such as Cd and Zn. In a number of embodiments, aqueous nitrate is reduced to nitrite using, for example, a water-soluble phenylthioether as a reducing agent in the presence of a water-soluble catalyst system. As described above, the phenylthioethers hereof may have the formula:

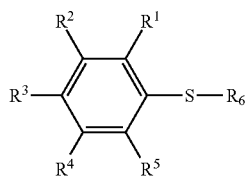

Wherein $R^1$ through $R^6$ are described above. Once nitrate is reduced to nitrite, the nitrite concentration is measured using a water soluble reagent system (for example, the Griess reagent system of FIG. 2 or a similar system) adapted to react with nitrite to generate a color. The color generation is then measured and correlated to nitrate concentration.

Figure 3:
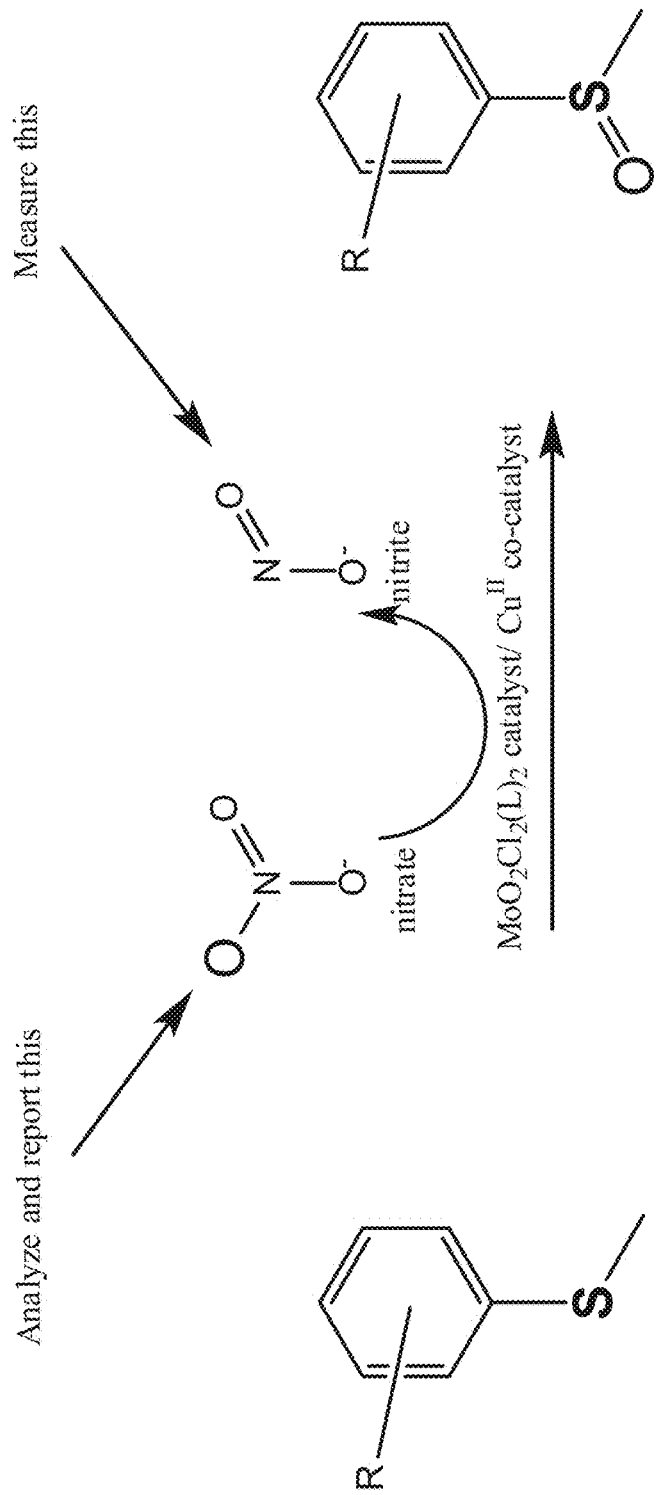
FIG. 3 shows the reduction of nitrate via water soluble thioether in the presence of a water soluble Mo catalyst/Cu (II) cocatalyst.

FIG. 3 illustrates an oxidation-reduction reaction in which nitrate is reduced to nitrite and a phenylthioether is oxidized to its corresponding sulfoxide in the presence of a Mo/$Cu^{2+}$ catalyst system. FIG. 2 illustrates a water soluble reagent system (a Griess assay reagent system) adapted to react with nitrite to generate a color. Griess assay reagents have different sensitivities. Depending on the test sensitivity required and nitrate concentrations to be measured, various Griess reagents may be used to give optimum results. Examples of azo dye agents suitable for use as Griess reagents include, but are not limited to, genistic acid, chronotropic acid, and N-alpha-naphthyl-ethylenediamine.

By choosing appropriate substituent group(s) for $R^1$, $R^2$, $R^3$, $R^4$, and/or $R^5$ in the general formula of a phenythioether hereof, the water solubility and reactivity/reaction kinetics of the thioether may be adjusted. To improve water solubility, hydrophilic substituent species are used. To improve reactivity/reaction kinetics with nitrate, $R^1$, $R^2$, $R^3$, $R^4$, and/or $R^5$ may be chosen to be electron density donating moieties that result in increased electron density at the sulfur atom via induction. $R^6$ is attached to the sulfur atom via a carbon atom and can vary widely. As described above, in a number of embodiments, is a $C_1$ to $C_6$ alkyl group or a polyalkyleneoxide (for example, polyethylene glycol). The polyalkyleneoxide may, for example, contain 4 to 5,000 carbon atoms or 20 to 1,000 carbon atoms.

In several embodiments, at least one of the $R^1$, $R^2$, $R^3$, $R^4$, or $R^5$ groups on the phenyl ring is a nitrogen-containing group and/or an oxygen-containing group. At least one of $R^1$, $R^2$, $R^3$, $R^4$, or $R^5$ may also be a charged group, which may increase the water solubility of the phenylthioether. For example, in a number of embodiments, one or more of $R^1$, $R^2$, $R^3$, $R^4$, and $R^5$ may be a charged sulfonate group. Such substituents may, for example, be made by reacting groups such as attached nitrogen-containing groups and/or oxygen-containing groups with sultones (that is, cyclic sulfonic esters) that ring open to form sulfonates, thereby resulting in even greater hydrophilicity/water solubility. Many other hydrophilic groups (for example, carboxylate groups) may be used to improve water solubility.

As set forth above, rate of reaction of, for example, a phenyl thioether with nitrate is dependent on the electron density of its aromatic ring. The higher the electron density on the ring, the faster the reaction rate and the higher the yield. High electron density on the phenyl ring creates higher electron density on the sulfur atom. The sulfur becomes more electron rich when electron density in the aromatic ring increases via electron induction. The more electron rich the sulfur is, the more likely it is to participate in oxidization reactions and oxygen transfer. The more electron rich the sulfur is, the better it is as a reductant.

Figure 4:
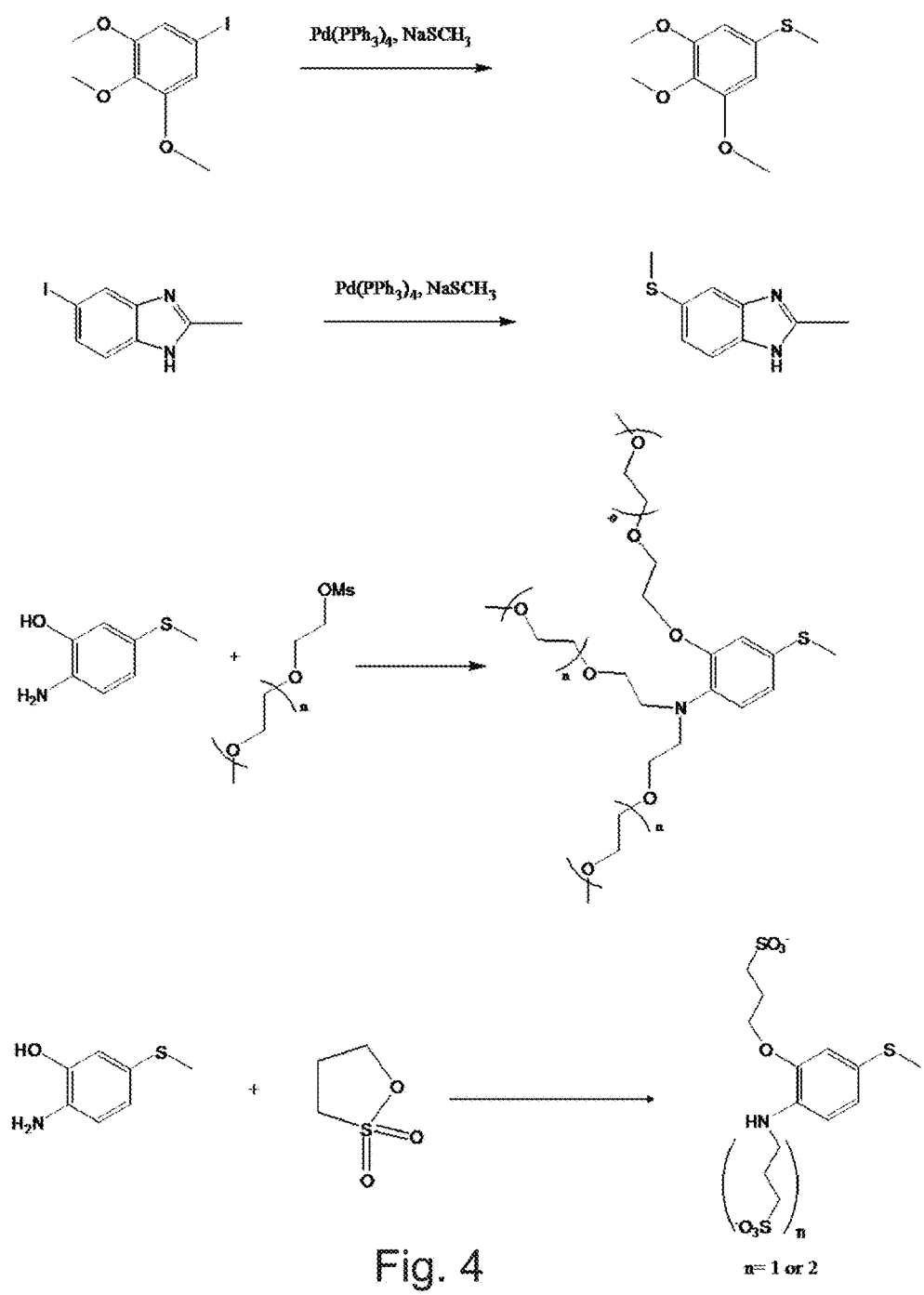
FIG. 4 illustrates a representative reaction scheme for synthesis of substituted phenylthioethers hereof.
Figure 5:
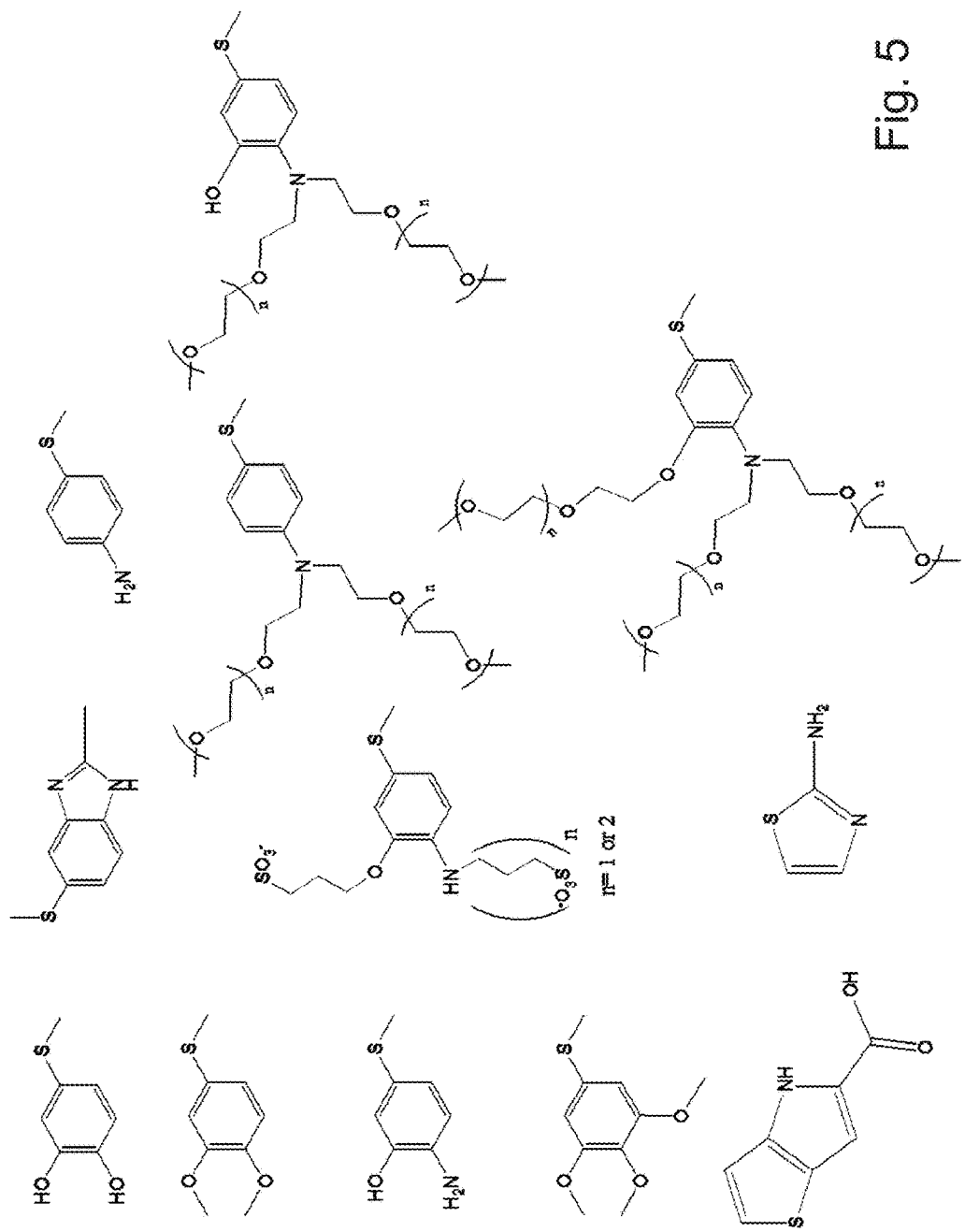
FIG. 5 illustrates representative examples of thioethers for use herein.

FIG. 4 illustrates a representative reaction scheme for synthesis of substituted phenylthioethers hereof. FIG. 5 illustrates representative examples of thioethers for use herein.

A water soluble catalyst was also synthesized. A molybdenum-based, water-soluble catalyst having the formula $MoO_2Cl_2(L)_2$ wherein L is a hydrophilic group was used in a number of embodiments. In several embodiments. L is a hydrophilic phosphine group. For example, L can be trisulfonated-triphenylphosphineoxide which is commercially available, for example, from Strem Chemical, Inc. of Newburyport, Mass. A water-soluble Mo catalyst was, for example, synthesized by mixing a small excess (for example, a 10% excess) of trisulfonated-triphenylphosphineoxide with a $MoO_2Cl_2$ complex at room temperature.

In addition to the water soluble Mo catalyst, a cocatalyst such as a water-soluble $Cu^{2+}$ cocatalyst can be used in the oxidation-reduction reaction. In a number of embodiments, the water-soluble $Cu^{2+}$ cocatalyst is $Cu(NO_3)_2$. Other water-soluble $Cu^{2+}$ cocatalysts include copper chloride ($CuCl_2$) and copper(II) sulfate ($Cu(SO_4)$).

The oxidation-reduction reaction, as shown in FIG. 3, proceeds directly with addition of the water-soluble Mo catalyst. Reaction rates are significantly faster when the $Cu^{2+}$ cocatalyst is used.

The thioether is sacrificial. It is not measured and can be present in large excess in the reagent systems hereof. As described above, the thioether may be designed for optimum reactivity and water solubility. To ensure complete reduction of nitrate, the molar amount of methylthioether used may, for example, be about a factor of 5-1000 greater than the analyte (nitrate), which is generally present at a maximum of about 15 ppmw. In a number of embodiments, the molar amount of methylthioether was about a factor of 10 greater than the analyte (nitrate). The homogeneous Mo catalyst may, for example, be used at about a 1:10 molar ratio compared to the thioether.

As described above, a colorimetric determination of nitrite ions can be made by reacting nitrite with aniline or an aniline derivative (like sulphanilic acid) in acidic medium to form a diazo salt (that is, the Griess assay or reagent system). The diazo salt is then reacted with an azo dye agent to form a colored azo dye. The solution's color intensity is directly proportional to nitrite concentration and thus directly related to nitrate concentration. The Griess reagents may, for example, be present in concentration or molar ratios as known in the art. Griess reagents may, for example, be present in large excess to the nitrite (for example, in a ratio of 10-100:1), but at approximately 1:1 molar ratio to each other.

Kits for determining nitrate concentration based on the above reagent systems and methodologies may be prepared. The kit may, for example, include an analysis system comprising a water soluble thioether chosen to reduce nitrate in the aqueous sample to nitrite, a water soluble catalyst, and a water soluble reagent system adapted to react with nitrite to generate a color, a system to measure a color generation, and a system to correlate the color generation to nitrate concentration. The water soluble thioethers, water soluble catalyst, and water soluble reagent system used in the kit are described above. The system to measure color generation may, for example, be a spectrometer, colorimeter, photometric device, color disc, color block, or the like. The system to correlate color generation to nitrate concentration may, for example, include a look-up table, color comparator, a processor system (for example, including a microcomputer or other computer), or the like. In several embodiments of a kit to determine nitrate concentration, a mobile or portable instrument is used.

An example of a portable instrument suitable for user in the kits hereof is set forth in U.S. Pat. No. 9,052,302, the disclosure of which is incorporated herein by reference. FIG. 6 schematically illustrates a mobile water-analyzing system 10 for a quantitative determination of a nitrate analyte in, for example, a water-sample. System 10 includes a basic unit 14 and a removable disposable test element 16 which is illustrated inserted into basic unit 14. Test element 16 is provided with a test-element body 18 made, for example, of a polymeric material. Test-element body 18 is provided with a sample-line 20 which may, for example, be formed as a groove. The side of the groove opening of test-element body 18 may be closed with a cover (for example, a plastic film or an aluminum cover, which is not shown).

Sample-line 20 is provided with an inlet opening 22 which is positioned at the distal end, referring to basic unit 14, and through which a water-sample is sucked from a water-reservoir 12. Adjacent to and, in the flow direction, behind inlet opening 22, is a meander-like mix section 26 of the sample-line 20 in which a reagent system as described herein and the drawn water-sample are homogeneously mixed.

A measuring section 28 is arranged adjacent to mix section 26 in which a quantitative determination may be performed. In a number of embodiments, measuring section 28 is a photometrical section, whereby measuring section 28 forms a measuring track for the respective photometrical/colorimetrical analyzer 30 of basic unit 14. Both sides of photometer/colorimeter section 28 may, for example, include a clear-transparent photometrical window 44, 46. Test-element body 18 may, for example, be fabricated from a clear transparent plastic which allows a measuring beam 35 to pass through measuring section 28.

Proximal to measuring section 28 (that is, behind measuring section 28 as seen from inlet opening 22), is a reagent section 23 with a dry reagent system 24 as described herein. At the sample-line end opposite to the inlet opening 22 (that is, behind the first reagent section 23), a pump opening 40 as a pump element is provided which is connected with a pump actuator of sample pump 42 of basic unit 14 when test element 16 is inserted into basic unit 14.

Basic unit 14 is provided with an analyzer 30 which may, for example, include a photometer/colorimeter with one or more light source (two light sources 32, 33 are provided in the illustrate embodiment) and a detector 34 in operative connection with a processing system/controller 50. Light-sources 32, 33 may, for example, emit light of different wavelengths.

Test element 16 is provided with a positioning element 48 such as an opening. Positioning element/opening 48 cooperates with a respective snap element of the basic unit 14 so that test element 16 is fixed reproducibly and accurately. Test element receptacle of basic unit 14 may, for example, be formed as a slot 15 in which the test element 16 fits without any clearance.

The water soluble reagents and catalyst hereof (collective, a reagent system) may, for example, be deposited on a test element such as test element 16, dried, and stored for later use. The test elements are insertable into a portable analysis system (as, for example, described above) to measure and correlate the color generation as described above. Multiple test elements hereof may be provided in a kit.

To reliably deposit reagents/catalysts on the test element, all components are preferably water soluble and are preferably in a homogeneous solution. The solutions are preferably homogeneous with no deposition on the walls and no crystallization. In general, to achieve a homogeneous solution each of the components should not be too close to the solubility limit therefor, and the components should dissolve readily in water. In some embodiments, the reagents/catalyst are deposited in 4-6 microliters of water and dried in an nitrogen filled oven.

The foregoing description and accompanying drawings set forth a number of representative embodiments at the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. A method of measuring nitrate concentration in an aqueous sample, comprising:
    a. mixing the aqueous sample with a water-soluble thioether chosen to reduce nitrate in the aqueous sample to nitrite in the presence of a water soluble catalyst, and a water soluble reagent system adapted to interact with nitrite to generate a color,
    b. measuring color generation, and
    c. correlating the color generation to nitrate concentration.

2. The method of claim 1 wherein the water-soluble thioether comprises a thioether-containing a five-membered, aromatic heterocyclic compound, a phenylalkyl thioether or a substituted phenylalkyl thioether.

3. The method of claim 1 wherein the water-soluble thioether has the formula:

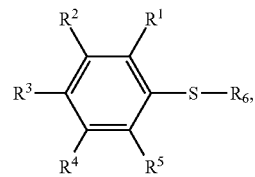

wherein $R^1$, $R^2$, $R^3$, $R^4$, and $R^5$ are selected independently from H, and a hydrophilic group or electron density donating group, wherein at least one of $R^1$, $R^2$, $R^3$, $R^4$, and $R^5$ is a hydrophilic or an electron density donating group, and wherein $R^6$ is selected from the group consisting of a $C_1$-$C_6$ alkyl group or a hydrophilic polymer.

4. The method of claim 3 wherein the hydrophilic polymer is a polyalkyleneoxide.

5. The method of claim 3 wherein at least one of $R^1$, $R^2$, $R^3$, $R^4$, and $R^5$ is —$OR^a$ wherein $R^a$ is selected from the group consisting of H, a $C_1$-$C_6$ alkyl group, a $C_1$-$C_6$ sulfonate terminated alkyl group, a phenyl group, and a polyalkylene oxide group, —$NR^bR^c$ wherein $R^b$ and $R^c$ are selected independently from the group consisting of H, a $C_1$-$C_6$ alkyl group, a $C_1$-$C_6$ sulfonate terminated alkyl group, and a polyalkylene oxide group, a dihydroxybenzene group, a phenyl diamine group, a phenyl diether group, a carboxylate group, and a polyalkyleneoxide group; or $R^1$ and $R^2$ together form a chain of four or five members selected from the group of CH, $CH_2$, NH, CC(O)OH or $NR^d$, wherein $R^d$ is an $C_1$-$C_6$ alkyl group or $C_1$-$C_6$ sulfonate terminated alkyl group; or $R^3$ and $R^4$ together form a chain of four or five members selected from the group of CH, $CH_2$, NH, CC(O)OH or $NR^d$.

6. The method of claim 4 wherein the phenyl diamine has the formula $C_6H_3(N(R^7)_2)(N(R^8)_2)$, wherein $R^7$ and $R^8$ are independently selected from the group consisting of hydrogen, $C_1$-$C_6$ alkyl group, a sulfonate terminated $C_1$-$C_6$ alkyl group, or a polylakyleneoxide group and the phenyl diether has the formula $C_6H_3(O(R^9))(O(R^{10}))$, wherein $R^9$ and $R^{10}$ are independently selected from the group consisting of hydrogen, $C_1$-$C_6$ alkyl group, a sulfonate terminated $C_1$-$C_6$ alkyl group, or a polylakyleneoxide group.

7. The method of claim 4 wherein the polyalkyleneoxide comprises 4 to 1000 carbon atoms.

8. The method of claim 1 wherein the water soluble catalyst comprises $MoO_2Cl_2(L)_2$ wherein L is a hydrophilic phosphine group.

9. The method of claim 8 wherein L comprises a triphenylphosphineoxide group.

10. The method of claim 8 wherein L is trisulfonated-triphenylphosphineoxide.

11. The method of claim 8 wherein the water soluble catalyst further comprises a $Cu^{2+}$ co-catalyst.

12. The method of claim 1 wherein the water soluble reagent system is a Griess reagent system.

13. The method of claim 1 wherein the water soluble reagent system comprises aniline or an aniline derivative and a receptor species chosen to form a chromophore with nitrite.

14. The method of claim 13 wherein the aniline derivative is chosen to form a diazonium salt with nitrite.

15. The method of claim 14 wherein the aniline derivative is sulphanilic acid.

16. The method of claim 13 wherein the receptor species comprises an azo dye agent.

17. The method of claim 16 wherein the receptor species is chosen from the group consisting of N-alpha-naphthyl-ethylenediamine, genistic acid, and chromotropic acid.

18. The method of claim 1 wherein the color generation occurs in the visible light spectrum.

19. The method of claim 1 wherein the color generation is measured using at least one of: a spectrometer, a colorimeter, a photometric device, a color disc, and a color block.

20. The method of claim 1 wherein the range of nitrate detection is between 0 and 15 ppmw.

* * * * *